United States Patent

Heckenberger

[11] Patent Number: 6,053,731
[45] Date of Patent: Apr. 25, 2000

[54] DEVICE FOR THE RECOGNITION OF CARIES, PLAQUE OR BACTERIAL INFECTION OF TEETH

[75] Inventor: Hans Heckenberger, Biberach, Germany

[73] Assignee: Kaltenbach & Voigt GmbH & Co., Germany

[21] Appl. No.: 09/036,475

[22] Filed: Mar. 6, 1998

[30] Foreign Application Priority Data

Mar. 7, 1997 [DE] Germany .................. 297 04 185 U

[51] Int. Cl.[7] .............. A61C 19/04; A61B 1/04
[52] U.S. Cl. ........................... 433/29; 600/477
[58] Field of Search ............. 433/92, 215; 600/477; 356/237.1, 317

[56] References Cited

U.S. PATENT DOCUMENTS

| | | |
|---|---|---|
| Re. 31,815 | 1/1985 | Alfano . |
| 4,479,499 | 10/1984 | Alfano ........................... 433/29 |
| 4,515,476 | 5/1985 | Ingmar ........................... 600/477 |
| 4,675,529 | 6/1987 | Kishida . |
| 5,055,048 | 10/1991 | Vassiliades et al. ........... 433/215 |
| 5,306,144 | 4/1994 | Hibst et al. ................... 433/215 |
| 5,382,163 | 1/1995 | Putnam . |
| 5,415,543 | 5/1995 | Rozmajzl, Jr. ................. 433/29 |
| 5,759,030 | 6/1998 | Jung et al. ..................... 433/26 |

FOREIGN PATENT DOCUMENTS

| | | |
|---|---|---|
| 0113152 | 7/1984 | European Pat. Off. . |
| 33 45 465 A1 | 6/1985 | Germany . |
| 30 31 249 C2 | 11/1986 | Germany . |
| 41 33 493 A1 | 7/1992 | Germany . |
| 90 07 569 | 11/1992 | Germany . |
| 42 00 741 A1 | 7/1993 | Germany . |
| 93 17 984 | 5/1995 | Germany . |
| 44 20 401 A1 | 12/1995 | Germany . |
| 44 33 123 C1 | 3/1996 | Germany . |
| 2-28543 | 1/1990 | Japan . |
| 5344982 | 12/1993 | Japan ........................... 433/29 |
| 2058343 | 4/1981 | United Kingdom . |

Primary Examiner—Ralph A. Lewis
Attorney, Agent, or Firm—Scully, Scott, Murphy & Presser

[57] ABSTRACT

Device for the recognition of caries, plaque or bacterial infection of teeth, the device having in substance a generator (4) for the generation of an excitation radiation (6) which with the aid of a dental handpiece (1) can be directed at a tooth (8) to be investigated, and a set of differently formed exchangeable emission and acquisition devices (2) for the irradiation of the tooth to be investigated with the excitation radiation (6) in dependence upon the surface of the tooth (8) to be treated in each case and for acquiring a fluorescence radiation (7) excited at the irradiated tooth (8). The individual exchangeable emission and acquisition devices (2) can each be removably coupled with the dental handpiece (1) and include a plurality of individual emission fibers (24a) and detection fibers (24b).

13 Claims, 4 Drawing Sheets

DEVICE FOR THE RECOGNITION OF CARIES, PLAQUE OR BACTERIAL INFECTION OF TEETH

BACKGROUND OF THE INVENTION

The invention relates to a device for the recognition of caries, plaque or bacterial infection of teeth.

Such a device is known for example from DE 30 31 249 C2. There, a tooth to be investigated is irradiated with a virtually monochromatic light source, whereby a fluorescence radiation is excited at the irradiated tooth. The fluorescence radiation thus excited at the tooth is acquired and evaluated, whereby in the fluorescence radiation clear differences appear as between carious and healthy tooth regions. Thus, in the red spectral region of the fluorescence spectrum of the tooth (ca. 550 to 650 nm) the intensity is significantly higher than with a healthy tooth. Thus, on the basis of the acquisition of the fluorescence radiation of the investigated tooth, a healthy tooth region can be unambiguously distinguished from a carious tooth region in a contactless manner.

A similar device for the recognition of caries is described in DE 42 00 741 A1, it being further proposed in this document to excite the fluorescence of the tooth by means of an excitation radiation having a wavelength in the range 360 to 580 nm and to filter out the thus obtained fluorescence radiation of the tooth for wavelengths from 620 nm. By means of these measures, the separation between the wavelength of the excitation radiation and the received fluorescence radiation is sufficiently large that the excitation radiation does not corrupt the evaluation results by superimposition on the fluorescence radiation.

Also from DE-U1-93 17 984 there is known a device for the recognition of caries whereby the excitation radiation is generated not continuously but pulsed, in an excitation interval. The fluorescence radiation of the investigated tooth brought about at the tooth due to the excitation radiation is acquired during an evaluation interval time-delayed with respect to the excitation interval.

From the above documents it is known only to irradiate a tooth to be investigated with a single light conductor and to detect the fluorescence radiation from the irradiated tooth by means of a detection light conductor arranged next to the emission light conductor. Thereby, however, non-homogeneous irradiation of the tooth to be investigated can occur and because of the arrangement of the detection light conductor next to the emission light conductor the fluorescence radiation is not precisely acquired.

SUMMARY OF THE INVENTION

The present invention thus has the object of so configuring a device for the recognition of caries, plaque or bacterial infection, that a tooth to be investigated can be homogeneously irradiated and the excited fluorescence radiation of the tooth can be precisely acquired. Further, the handling of the overall device, and its field of application, are to be improved.

The object is achieved in accordance with the invention by means of the claimed device for the recognition of caries, plaque or bacterial infection.

In accordance with the invention, the emission and acquisition device has a plurality of individual emission fibers and detection fibers, which can be arranged alternating with one another, whereby the number of emission fibers and detection fibers may in general be between 1 and x. In particular, only one emission fiber may be coaxially surrounded by a plurality of detection fibers. The individual fibers of the fiber light conductor bundle of the emission and acquisition device, which as a rule is will be provided by a removable light probe, are surrounded by a sheathing which for example may be manufactured of metal or plastics. The sheathing protects the individual fibers of the fiber light conductor bundle from damage and breakage, so that by means of this additional protection the handling of the emission and acquisition device, i.e. the light probe, is improved.

The light probe serving as emission and acquisition device is removably coupled with a dental handpiece with the aid of which the light probe can be directed towards a tooth to be investigated. Also the dental handpiece has an internal light conductor system which, with the light probe put in place, is coupled with the light conductor fibers of the light probe. In particular the dental handpiece has central emission light conductor which is coaxially surrounded by a plurality of individual detection light conductor fibers. In accordance with an advantageous embodiment, the single emission light conductor fiber of the dental handpiece is surrounded by nine detection light conductor fibers so that with a emission light conductor fiber diameter of 0.5 mm and a detection light conductor fiber diameter of 0.25 mm there is provided a virtually closed ring cross-section with a diameter of 1 mm.

The sensitivity for the acquisition of the fluorescence radiation excited at the irradiated tooth depends in substance upon the configuration of the light probe serving as acquisition device. Thus, for example, with a rounded or truncated cone like light probe tip a significantly greater sensitivity can be achieved.

The irradiation of a tooth to be investigated is effected advantageously with an excitation light the wavelength of which lies in the range 600–670 nm. In particular, the wavelength of the excitation light is 655 nm.

Since the light probe serving for the emission of the excitation light and for detection of the excited fluorescence spectrum is configured to be removable from the dental handpiece, in dependence upon the field of application in each case, i.e. in dependence upon the tooth region to be investigated, the correspondingly appropriate light probe can be selected from a set of exchangeable light probes and inserted on to the dental handpiece.

BRIEF DESCRIPTION OF THE DRAWINGS

The invention will be described below with reference to preferred exemplary embodiments and with reference to the accompanying drawings, which show.

DETAILED DESCRIPTION OF THE PREFERRED EMBODIMENTS

Figure 1:
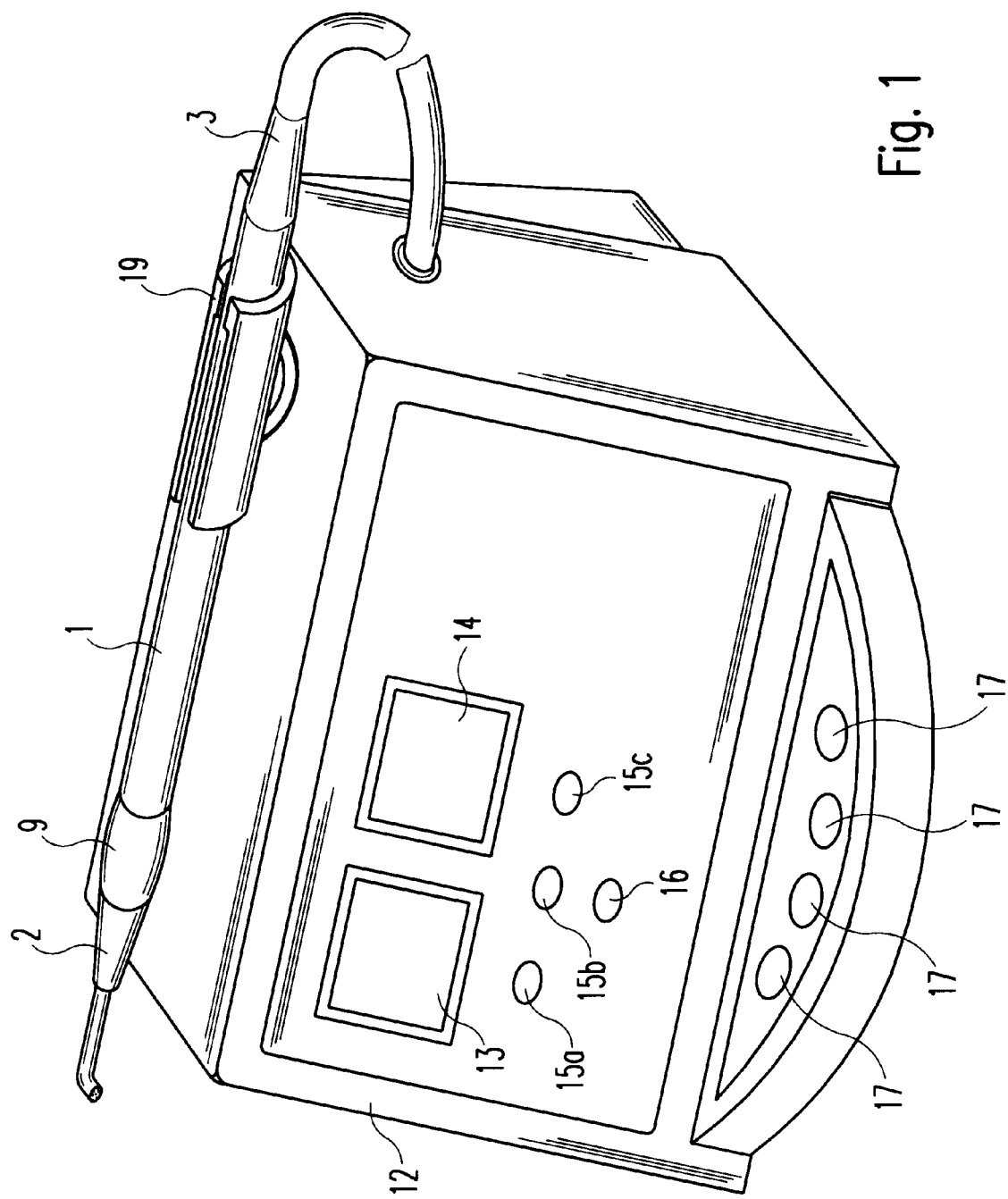
FIG. 1 an overall view of the device in accordance with the invention for the recognition of caries, plaque or bacterial infection, FIG. 2 a block diagram which indicates the manner of functioning of the device in accordance with the invention shown in FIG. 1, FIG. 3 a partial cross-sectional view of the dental handpiece and the light probe which are employed with the device in accordance with the invention shown in FIG. 1, and cross-sectional views of three different light probe forms, FIG. 4 a more detailed cross-sectional view of the light probe illustrated in FIG. 3b, which is employed with the device in accordance with the invention shown in FIG. 1, FIG. 5 a sectional view along the chain line shown in FIG. 4, whereby the light conductor fiber arrangement provided by FIG. 5 may also correspond to the light conductor fiber arrangement in the dental handpiece shown in FIG. 3a, and FIG. 6 a sectional view, similar to the view illustrated in FIG. 5, of the light probe in accordance with a further exemplary embodiment.

FIG. 1 shows an overall view of the device in accordance with the invention for the recognition of caries, plaque or bacterial infection.

The device in accordance with the invention includes a central unit 12 to which a dental handpiece 1, having a light probe 2 which can be inserted on to the dental handpiece, is connected via a supply hose 3. The central unit 12 contains a laser light source which serves as excitation light for investigation of a tooth. For the irradiation of the tooth to be investigated with excitation light and for the acquisition of the fluorescence radiation coming from the tooth to be investigated, the light conductor system connecting the light probe 2 with the central unit 12 has at least one emission light conductor fiber which directs the excitation light from the central unit 12 to the light probe, and a plurality of detection fibers which acquire the fluorescence spectrum of the irradiated tooth and direct it back from the light probe 2 to the central unit 12.

Figure 2:
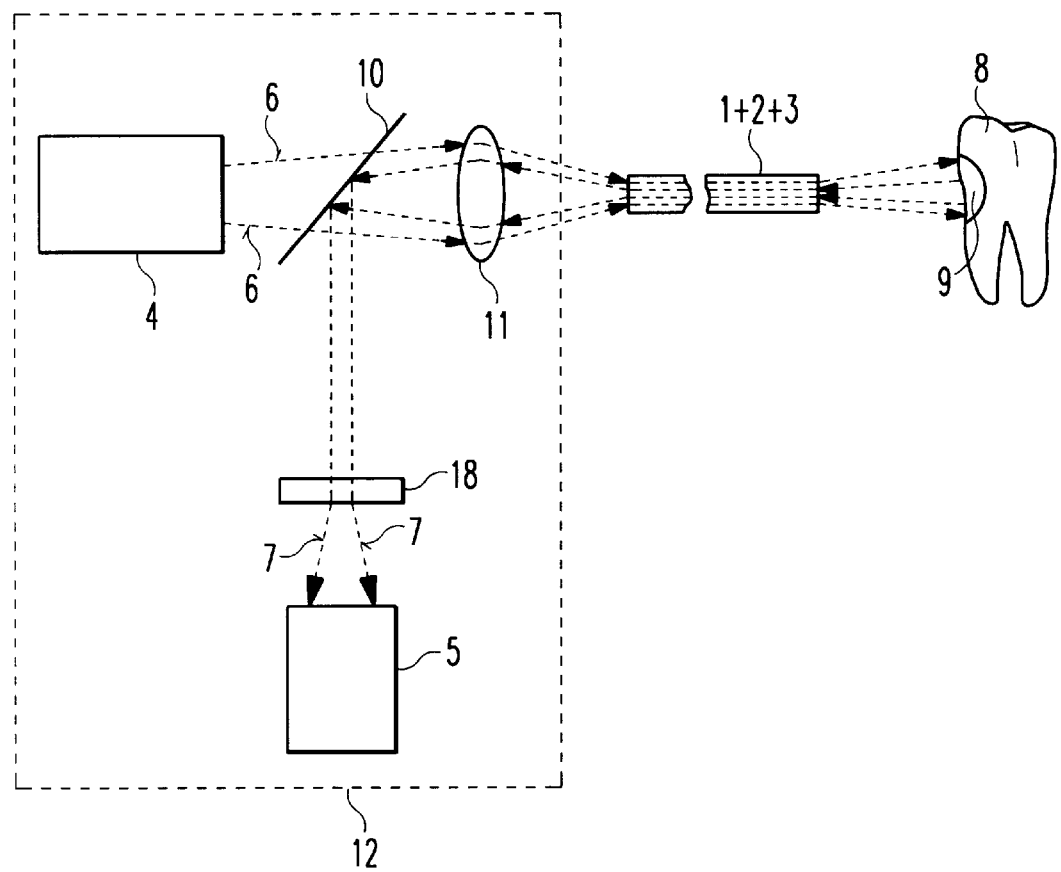

The manner of functioning of the device in accordance with the invention is thereby clear from the block circuit diagram shown in FIG. 2. The central unit 12 includes a light source 4 for the generation of an excitation radiation 6 and an evaluation and acquisition device 5 for acquiring, displaying and if appropriate evaluating the fluorescence radiation 7 excited at the tooth 8. The excitation radiation 6 generated by the light source 4 is delivered via a coupling lens system 11 to the light conductor system consisting of the supply hose 3, the dental handpiece 1 and the light probe 2. The light probe 2 irradiates a region 9 of the tooth 8 to be investigated with the excitation radiation, the wavelength of which advantageously lies in the range 600 nm to 670 nm. The detection fibers of the light probe 2 detect the fluorescence radiation of the tooth 8, which radiation is delivered to the evaluation and acquisition device 5 via a beam divider 10 and a spectral filter 18. The spectral filter 18 is thereby advantageously so configured that it passes only fluorescence radiation with a wavelength greater than 670 nm. The evaluation and acquisition device 5 evaluates the fluorescence radiation 7 delivered thereto directly and determines directly from the acquired fluorescence radiation either the presence or absence of caries, plaque or bacterial infection. The light source 4 is preferably a HeNe laser or a laser diode. The excitation radiation has in particular a wavelength of ca. 655 nm, since at this wavelength there can be achieved the best possible compromise between the available output power, which increases with increasing wavelength, and the spectral difference between the excitation radiation and the fluorescence radiation, which decreases with increasing excitation wavelength. The spectral filter 18 has a pass band from 670 nm, since with the proposed excitation wavelength range between 600 nm and 670 nm the fluorescence radiation of the tooth having wavelengths greater than 670 nm has the maximum difference between the fluorescence intensities for carious regions and the fluorescence intensities for healthy tooth regions.

The device in accordance with the invention shown in FIG. 1 has further two display regions 13, 14, whereby the display 13 displays the instantaneous measurement value of the fluorescence radiation and the display 14 displays the peak value occurring during the measurement. Through the continuous display of the peak value of the fluorescence radiation by the display 14, the dentist can, in the treatment of a patient, find again the location with the highest incidence of caries by means of comparison of the two displays 13 and 14. Further, the device in accordance with the invention has three displays 15a–c which indicate, by lighting up, the selected light probe 2 of the three different available light probes. In order to reduce the weight of the device in accordance with the invention, and to increase the mobility of the device, the device is preferably operated with a battery or accumulator, whereby the display 16 displays, by lighting up, the fall of the supply voltage delivered by the battery or accumulator below a limit voltage value. In this event, the user is requested, by lighting up of the display 16, to exchange the battery or to charge the accumulator anew. Finally, the device shown in FIG. 1 has a plurality of keys 17 for the calibration of the device in accordance with the invention before it is put into operation and for the selection of particular predetermined modes of operation. Further, by way of the keys 17, the type of light probe 2 inserted on the dental handpiece 1 can be indicated to the central unit 12. In particular for fixing the dental handpiece 1 during the transportation of the device in accordance with the invention a storage holder 19 is provided, which may be constituted to be rotatable in steps or steplessly and which may also be applied to the side on the central unit 12. A ring switch 9 is attached to the dental handpiece 1. This ring switch 9 corresponds to a ring-shaped switch extending in the circumferential direction of the dental handpiece 1, so that the operating person can switch the device according to the invention on or off by pressing with only one finger, independently of the disposition of the dental handpiece 1 in the person's hand. Further, via the ring switch 9, by a short press, the peak value displayed by the display 14 can be deleted and by a long press a new reference value can be set, i.e. the light probe can be equalized.

FIG. 2 shows a partial cross-sectional view of the supply hose 3 with the dental handpiece 1 and a light probe 2 which can be inserted on to the dental handpiece 1, of the device for the recognition of caries shown in FIG. 1. Both the light probe 2 and also the hose connection of the supply hose 3 can be inserted on to the dental handpiece 1. The handpiece 1 has an internal channel 20, in which the light conductor system connecting the hose 3 and the light probe 2 is mounted. The light probe 2 has a channel 21 arranged in a rigid sleeve 22, in which the emission and detection fibers run. In accordance with the invention, in dependence upon the properties of the tooth region to be investigated, a selection can be made from a plurality of predetermined light probe types. Thus, FIG. 3b shows the cross-section of a light probe tip for the investigation of smooth tooth surfaces, FIG. 3c the cross-section of a light probe tip for the investigation of fissures, whereby the tooth end of this light conductor probe is rounded or truncated cone like, and FIG. 3d a light conductor probe for the investigation of approximal regions (spaces between teeth) of a tooth, whereby the end of this light conductor probe is pointed.

Figure 3:
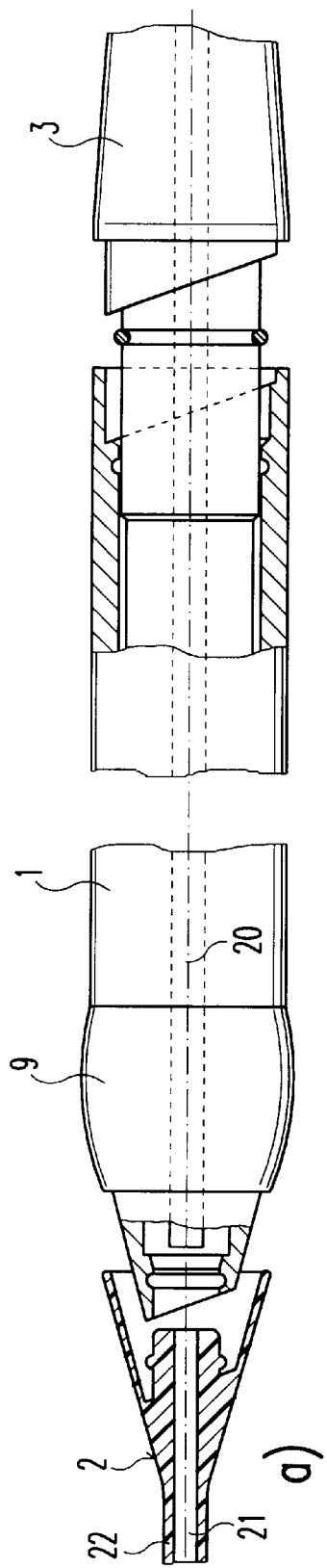
Figure 4:
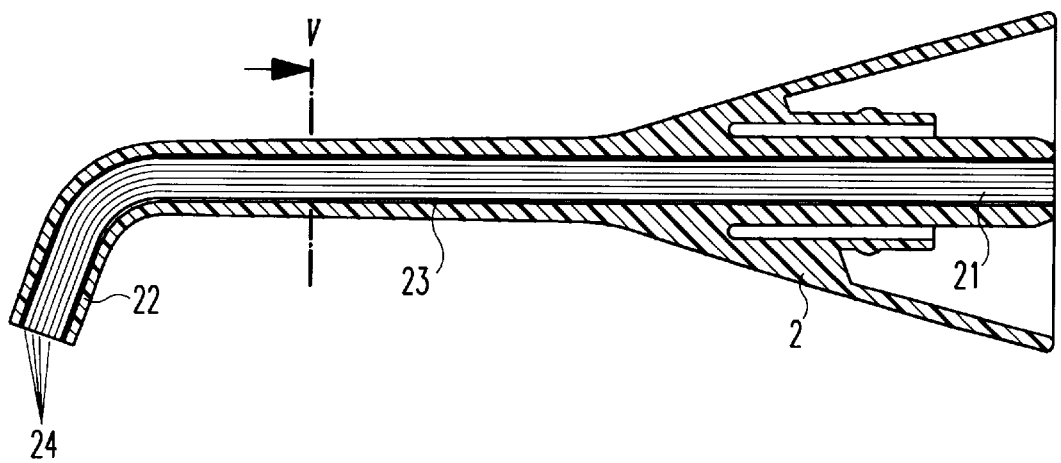
Figure 5:
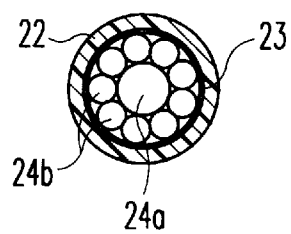

FIG. 4 shows a cross-sectional view through the light conductor probe shown in FIG. 3, with light conductor fibres guided therein. As can be seen from FIG. 4, a plurality of individual light conductor fibers 24 are guided in the light conductor channel 21 of the light conductor probe 2. Of the individual light conductor fibers 24, some serve for transmission of the excitation light and others for detection of the fluorescence radiation radiated from the tooth to be investigated. The arrangement of the excitation light conductor fibers relative to the detection light conductor fibers is thereby not initially fixed. However, in order to be able to achieve an irradiation of the tooth to be investigated which is as homogeneous as possible, and to attain a acquisition of the excited fluorescence radiation which is as uniform and exact as possible, it is advantageous to arrange the excitation light conductor fibers and detection light conductor fibers alternating with one another. In particular the individual light conductor fibers can be arranged in the light conductor channel 21 as shown in FIG. 5, whereby a plurality of detection light conductor fibers 24b are arranged concentrically around an emission light conductor fiber 24a. In this way the reliability and exactitude of acquisition can be increased or stabilised. In accordance with FIGS. 4 and 5, the light conductor fibers are arranged in a sleeve 22 which can be manufactured for example of metal or plastics or any other suitable material. Further, the light conductor fibers are also surrounded by a sheathing 23. By this sheathing the danger of damage to the fiber bundle guided in the light conductor channel 21 is reduced and breakage of the individual light conductor fibers prevented.

As already explained with reference to FIG. 3, the internal channel 20 of the dental handpiece 1 shown in FIG. 3 also has a plurality of individual light conductor fibers which either carry the excitation light to the light conductor probe or carry back the fluorescence radiation acquired by the light conductor probe 2 to the evaluation and determination device. Thereby, after placing of the light conductor probe 2 on the dental handpiece 1, the light conductor fibers guided in the light conductor channel 21 of the light conductor probe are connected with the light conductor fibers guided in the channel 20 of the dental handpiece 1. In particular, the light conductor system guided in the light conductor channel 20 of the dental handpiece 1 can have the arrangement of individual light conductor fibers shown in FIG. 5, i.e. in the light conductor channel 20 there is present only one central emission light conductor fiber 24a for transmitting the excitation light, a plurality of individual detection light conductor fibers 24b being arranged coaxially around the emission light conductor fiber 24a. If for example—as shown in FIG. 5—nine detection light conductor fibers with a fiber diameter of 0.25 mm are coaxially arranged around a emission light conductor fiber with a diameter of 0.5 mm, there is provided a virtually closed ring cross-section with a diameter of 1 mm.

In conclusion, however, attention is directed to the fact that the arrangement of the light conductor fibers in the light probe 2 need not necessarily correspond to the arrangement of the light conductor fibers in the dental handpiece. Rather, it is only necessary that, after placing the light conductor probe 2 on the dental handpiece 1, the emission light conductor fibers or detection light conductor fibers guided in the light probe 2 be connected with the corresponding emission light conductor fibers or detection light conductor fibers of the dental handpiece 1 by means of an appropriate coupling mechanism. Thus, for example, the dental handpiece may have the light conductor arrangement shown in FIG. 5 whilst the light conductor probe 2 has not just one but a plurality of emission light conductor fibers which are arranged alternatingly with the corresponding detection light conductor fibers, whereby these plural emission light conductor fibers are coupled with the central emission light conductor fiber 24a, shown in FIG. 5, of the dental handpiece. Thus, it is also possible that the diameter of the fiber light conductor bundle of the light conductor probe is larger than the corresponding fiber light conductor bundle diameter of the dental handpiece. In particular, the diameter of the fiber light conductor bundle of the light conductor probe may be greater than 1 mm.

Figure 6:
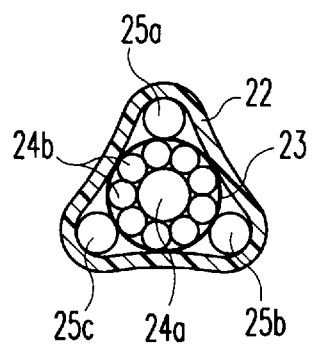

FIG. 6 shows a further sectional view of a light probe employed with the device in accordance with the invention. In this case the individual light conductor fibers 24a, 24b are surrounded by three tubes 25a–25c evenly distributed in the circumferential direction of the light probe, which are made of tough material, for example metal, and thus serve for stabilisation of the light probe. The tubes 25a–25c may for example be surrounded by a flexible shrink-on hose 22, or other, since already due to the tube arrangement a sufficient stability and a sufficient protection of the light conductor fibers is ensured. Further, the tubes 25a–25c may also be arranged inside the fixed sheathing 22 of the light probe illustrated in FIG. 5. Advantageously, the tubes serve not only as stabilisation means for the light probe but also for the delivery of operating media which are necessary or suitable for the operation of the device in accordance with the invention or of the light probe, such as for example illuminating light or spray air. In particular the delivery of spray or blasting air via the tubes 25a–25c is of assistance since it has proved that a more reliable measurement result can be achieved when the location of the tooth which is to be investigated has been blasted clean or dry.

What is claimed is:

1. A device for detecting the presence of carries, plaque or bacterial infection on teeth, the device comprising:
    means for generating excitation radiation;
    a dental handpiece coupled to the generating means for receiving the excitation radiation therefrom and for directing said radiation away therefrom;
    a set of exchangeable light probe tips, each of the light probe tips being removably coupled with the dental handpiece for receiving the excitation radiation therefrom and for directing said radiation onto a region of a tooth, wherein fluorescence radiation is reflected by the tooth, and each of said light probe tips includes at least one individual emission fiber for receiving said excitation radiation from said dental handpiece and directing said excitation radiation onto said region of said tooth and a plurality of detection fibers for receiving said fluorescence radiation from said tooth and for conducting said fluorescence radiation to said dental handpiece, and wherein the light probe tip that is to be removably coupled with the dental handpiece is selected in dependence upon the surface property of the tooth region; and
    evaluation means coupled to the dental handpiece for receiving and evaluating the fluorescence radiation from the handpiece to identify carries, plaque or bacterial infection on said region of the tooth; and wherein each light probe tip (2) has at least one tube (25a, 25b, 25c) extending along the longitudinal direction of the light probe tip to stabilize the light probe tip.

2. Device according to claim 1,
characterized in that,
    the individual fibers (24, 24a, 24b) of each light probe tip are surrounded by a sheathing (22).

3. Device according to claim 2,
characterized in that,
    the sheathing (22) is manufactured of metal or plastics.

4. Device according to claim 1,
characterized in that,
    each light probe tip (2) has a plurality of tubes (25a, 25b, 25c), substantially uniformly distributed around the circumference of the light probe tip, and extending along the longitudinal direction of the light probe tip to stabilize the light probe tip.

5. Device according to claim 1, characterized in that, said at least one tube (25*a*, 25*b*, 25*c*) also delivers an operating medium for the operation of the device.

6. A device according to claim 5, wherein said at least one tube delivers blasting air.

7. Device according to claim 1, characterized in that, the detection fibres (24*b*) are arranged concentrically around the emission fiber (24*a*) for receiving the fluorescence radiation (7), and whereby after coupling of one of the light probe tips (2) with the dental handpiece (1), the emission and detection fibers of the respective light probe tip (2) are coupled with the emission and detection fibers of the dental handpiece (1).

8. Device according to claim 7, characterized in that, the dental handpiece (1) has nine detection fibers (24*b*), each of a diameter of 0.25 mm, arranged concentrically around the emission fiber (24*a*), the emission fibre (24*a*) of the dental handpiece (1) having a diameter of 0.5 mm.

9. Device according to claim 1, characterized in that, the plurality of detection fibers (24*b*) are arranged concentrically around the emission fiber (24*a*).

10. Device according to claim 1, characterized in that, the individual emission and detection fibers of each light probe tip (2) form a fiber bundle having a diameter greater than 1 mm.

11. Device according to claim 1, characterized in that, the wavelength of the excitation radiation is in the range between 600 and 670 nm.

12. A device according to claim 11, wherein the excitation radiation has a wavelength of 655 nm.

13. Device according to claim 1, characterized in that, the set of light probe tips (2) includes one light probe tip for the investigation of smooth tooth surfaces, one light probe tip for the investigation of fissures, and one light probe tip for the investigation of spaces between teeth.

* * * * *